US009757053B2

(12) United States Patent
Richards

(10) Patent No.: US 9,757,053 B2
(45) Date of Patent: Sep. 12, 2017

(54) PHOTO SCALING GUIDE CONFIGURED TO SCALE WOUNDS OR OBJECTS

(71) Applicant: Thomas J. Richards, Chino Hills, CA (US)

(72) Inventor: Thomas J. Richards, Chino Hills, CA (US)

( * ) Notice: Subject to any disclaimer, the term of this patent is extended or adjusted under 35 U.S.C. 154(b) by 147 days.

(21) Appl. No.: 14/567,907

(22) Filed: Dec. 11, 2014

(65) Prior Publication Data

US 2015/0089994 A1 Apr. 2, 2015

Related U.S. Application Data

(63) Continuation-in-part of application No. 13/405,555, filed on Feb. 27, 2012, now Pat. No. 8,939,918, which is a continuation of application No. 12/069,045, filed on Feb. 7, 2008, now Pat. No. 8,123,704.

(60) Provisional application No. 61/921,350, filed on Dec. 27, 2013.

(51) Int. Cl.
| | |
|---|---|
| *A61B 5/103* | (2006.01) |
| *A61B 5/117* | (2016.01) |
| *G01B 3/00* | (2006.01) |
| *G01B 3/14* | (2006.01) |
| *B43L 13/20* | (2006.01) |
| *B43L 7/00* | (2006.01) |
| *A61B 5/107* | (2006.01) |
| *G01D 13/00* | (2006.01) |
| *G01B 21/02* | (2006.01) |
| *A61B 5/00* | (2006.01) |

(52) U.S. Cl.
CPC ............ *A61B 5/107* (2013.01); *A61B 5/1075* (2013.01); *A61B 5/445* (2013.01); *A61B 5/7445* (2013.01); *G01B 21/02* (2013.01); *G01D 13/00* (2013.01); *A61B 5/6832* (2013.01)

(58) Field of Classification Search
CPC ......... A61B 5/107; G01D 13/00; G01B 21/02
See application file for complete search history.

(56) References Cited

U.S. PATENT DOCUMENTS

| | | | | | |
|---|---|---|---|---|---|
| 1,062,525 | A | * | 5/1913 | Ward ........................ | G01B 3/34 33/514.1 |
| 1,667,802 | A | * | 5/1928 | Homan, Jr. ............... | A43D 1/02 33/3 A |
| 2,049,245 | A | * | 7/1936 | Breitbarth ............... | B43L 13/08 33/1 B |
| 2,346,219 | A | * | 4/1944 | Johnson ................. | B42D 15/00 156/DIG. 33 |
| 2,478,071 | A | * | 8/1949 | Agrillo ................. | B43L 13/205 33/565 |
| 2,500,873 | A | * | 3/1950 | Sager ....................... | G11B 3/34 33/563 |
| 2,574,152 | A | * | 11/1951 | Lewis ................ | B65D 63/1009 206/411 |
| 3,906,639 | A | * | 9/1975 | Wilamowski ............ | G01B 3/16 33/27.03 |
| 3,912,270 | A | * | 10/1975 | Trossman ............. | A63F 3/0005 273/245 |
| 4,131,998 | A | * | 1/1979 | Spears ................... | A61B 5/107 33/1 BB |

(Continued)

*Primary Examiner* — Sean Dougherty
(74) *Attorney, Agent, or Firm* — Larry K. Roberts

(57) ABSTRACT

A photo scaling guide or system configured to scale both the area and linear dimensions of wounds or objects at the same time with one device.

18 Claims, 10 Drawing Sheets

(56) References Cited

U.S. PATENT DOCUMENTS

| | | | | |
|---|---|---|---|---|
| 4,219,029 A * | 8/1980 | Grossman | A61B 5/1073 | 33/2 R |
| D266,820 S * | 11/1982 | Ferrin | D10/46.3 | |
| 4,389,782 A * | 6/1983 | Webster | A61B 5/441 | 283/115 |
| 4,462,168 A * | 7/1984 | Lynch | B43L 7/005 | 33/1 N |
| 4,485,585 A * | 12/1984 | Shackelford | A63F 9/06 | 434/258 |
| 4,719,925 A * | 1/1988 | Parsons | A61B 5/435 | 33/512 |
| 4,982,627 A * | 1/1991 | Johnson | B23B 31/005 | 81/121.1 |
| 5,051,259 A * | 9/1991 | Olsen | A61F 5/445 | 424/443 |
| 5,106,629 A * | 4/1992 | Cartmell | A61F 13/0203 | 424/443 |
| 5,264,218 A * | 11/1993 | Rogozinski | A61F 13/023 | 424/443 |
| 5,265,605 A * | 11/1993 | Afflerbach | A61B 5/107 | 600/300 |
| D348,618 S * | 7/1994 | Leslie | D10/64 | |
| 5,330,230 A * | 7/1994 | Craig | G09F 3/00 | 283/55 |
| 5,364,200 A * | 11/1994 | Russo | B42F 3/006 | 283/105 |
| 5,414,943 A * | 5/1995 | Vogt | A61B 5/107 | 33/512 |
| 5,450,678 A * | 9/1995 | Check | G01B 5/0023 | 116/200 |
| 5,527,111 A * | 6/1996 | Lysen | G01K 1/16 | 136/221 |
| 5,577,328 A * | 11/1996 | Kerry, Sr. | G01B 3/14 | 33/1 G |
| 5,588,428 A * | 12/1996 | Smith | A61B 5/1077 | 382/128 |
| 5,618,292 A * | 4/1997 | Poler | A61B 19/54 | 33/512 |
| 5,741,212 A * | 4/1998 | Matthews | A61B 5/1034 | 33/512 |
| 5,807,281 A * | 9/1998 | Welch | A61B 5/435 | 600/588 |
| 5,884,408 A * | 3/1999 | Simmons | G01B 3/02 | 33/494 |
| 5,967,979 A * | 10/1999 | Taylor | A61B 5/0059 | 356/613 |
| 6,044,572 A * | 4/2000 | Sore | G01B 3/02 | 33/529 |
| 6,066,104 A * | 5/2000 | Dao | A61B 5/435 | 600/588 |
| 6,159,167 A * | 12/2000 | Hardin-Naser | A61B 5/445 | 33/512 |
| 6,216,354 B1 * | 4/2001 | Carbone | B43L 13/20 | 33/27.01 |
| 6,279,244 B1 * | 8/2001 | Kelley | A44C 9/02 | 33/512 |
| 6,286,224 B1 * | 9/2001 | Lewis | G01B 3/14 | 33/512 |
| 6,321,457 B1 * | 11/2001 | Lariviere, Jr. | B26B 29/06 | 33/562 |
| 6,446,571 B1 * | 9/2002 | Sloot | E01F 9/015 | 116/209 |
| 6,471,661 B1 * | 10/2002 | Burns | A61B 5/1077 | 33/512 |
| 6,489,760 B2 * | 12/2002 | Kim | G01B 7/001 | 318/657 |
| 6,609,309 B2 * | 8/2003 | Shibuya | G01D 5/165 | 33/1 PT |
| 6,640,460 B1 * | 11/2003 | Nabarro | A41O 5/00 | 33/512 |
| D499,029 S * | 11/2004 | Maarberg | D10/46.3 | |
| 6,820,478 B1 * | 11/2004 | Nabarro | A41O 5/00 | 73/149 |
| 6,857,196 B2 * | 2/2005 | Dalrymple | G01B 3/30 | 33/512 |
| 6,893,422 B2 * | 5/2005 | Altman | A61F 15/004 | 128/846 |
| 6,895,808 B2 * | 5/2005 | Remmlinger | G01M 13/02 | 324/204 |
| 6,917,895 B2 * | 7/2005 | Paanasalo | B65H 18/26 | 702/155 |
| 7,032,413 B1 * | 4/2006 | Specktor | D04B 3/00 | 33/555.2 |
| 7,117,765 B1 * | 10/2006 | Wallden | B25B 13/56 | 81/52 |
| 7,150,108 B2 * | 12/2006 | Babb | A61B 5/435 | 33/511 |
| 7,242,197 B2 * | 7/2007 | Satou | G01R 15/183 | 324/522 |
| 7,401,413 B1 * | 7/2008 | Nelson | A61B 5/107 | 128/897 |
| 7,566,057 B2 * | 7/2009 | Mascolo | A63F 9/0073 | 273/153 J |
| D599,416 S * | 9/2009 | Turco-Rivas | D21/471 | |
| 7,707,736 B2 * | 5/2010 | Keenan | A61B 17/32 | 33/27.01 |
| 7,772,454 B2 * | 8/2010 | Addison | A61F 13/00063 | 424/445 |
| 7,790,946 B2 * | 9/2010 | Mulligan | A61F 13/0203 | 602/41 |
| D634,009 S * | 3/2011 | Lam | D24/140 | |
| 8,276,287 B2 * | 10/2012 | Estocado | A61B 5/1072 | 33/1 BB |
| 2001/0042982 A1 * | 11/2001 | McClure | G11B 23/40 | 283/81 |
| 2002/0115954 A1 * | 8/2002 | Worthley | A61F 13/02 | 602/57 |
| 2003/0153860 A1 * | 8/2003 | Nielsen | A61F 13/02 | 602/43 |
| 2003/0219469 A1 * | 11/2003 | Johnson | A61L 15/40 | 424/445 |
| 2005/0101961 A1 * | 5/2005 | Huebner | A61B 17/8605 | 606/304 |
| 2006/0053162 A1 * | 3/2006 | Ueda | G06K 1/123 | |
| 2006/0058721 A1 * | 3/2006 | Lebner | A61F 13/023 | 602/42 |
| 2006/0100739 A1 * | 5/2006 | Raffle | B25J 9/08 | 700/245 |
| 2006/0174505 A1 * | 8/2006 | Chang | B23Q 16/001 | 33/645 |
| 2007/0066946 A1 * | 3/2007 | Haggstrom | A61M 1/0031 | 604/313 |
| 2008/0008370 A1 * | 1/2008 | Chio | A61B 5/441 | 382/128 |
| 2009/0084179 A1 * | 4/2009 | Gougian | G01F 19/00 | 73/427 |
| 2009/0204028 A1 * | 8/2009 | Richards | A61B 5/445 | 600/587 |
| 2010/0004564 A1 * | 1/2010 | Jendle | A61B 5/107 | 600/587 |
| 2011/0230313 A1 * | 9/2011 | Gamboa | A63B 22/20 | 482/51 |
| 2013/0115848 A1 * | 5/2013 | Silverglate | A63H 33/04 | 446/124 |

* cited by examiner

PHOTO SCALING GUIDE CONFIGURED TO SCALE WOUNDS OR OBJECTS

CROSS-REFERENCE TO RELATED APPLICATIONS

This application claims priority to U.S. Provisional Application No. 61/921,350, filed Dec. 27, 2013, is a continuation-in-part of U.S. application Ser. No. 13/405,555, filed Feb. 27, 2012, which in turn is a continuation of U.S. application Ser. No. 12/069,045 filed Feb. 7, 2008, now U.S. Pat. No. 8,123,704; the entire contents of which applications are hereby incorporated by reference.

BACKGROUND

This invention relates generally to the field of wound calibration and measurement in hospitals and all other medical settings, and in forensic and accident investigations.

The treatment of wounds is often dependent upon rapid assessment of the nature of the wound. Size in terms of the area, or the length of the wound, is often critical. An accurate description and assessment of the measured wound allows for documentation of demonstrated healing and possibly reduce legal liabilities. Hospitals, nursing homes, home health care and military field hospitals are examples of assessing wound size initially and through the progression of the healing process of the wound. Furthermore, SB 1301 mandated all acute care hospitals to report stage 3 and stage 4 wounds to state licensing agencies. When these state agencies investigate the wound, accurate wound size is imperative to demonstrate healing.

DETAILED DESCRIPTION

Detailed descriptions of the preferred embodiment are provided herein. It is to be understood, however, that the present invention may be embodied in various forms. Therefore, specific details disclosed herein are not to be interpreted as limiting, but rather as a basis for the claims and as representative basis for teaching one skilled in the art to employ the present invention in virtually any appropriately detailed system, structure or manner.

Figure 1:
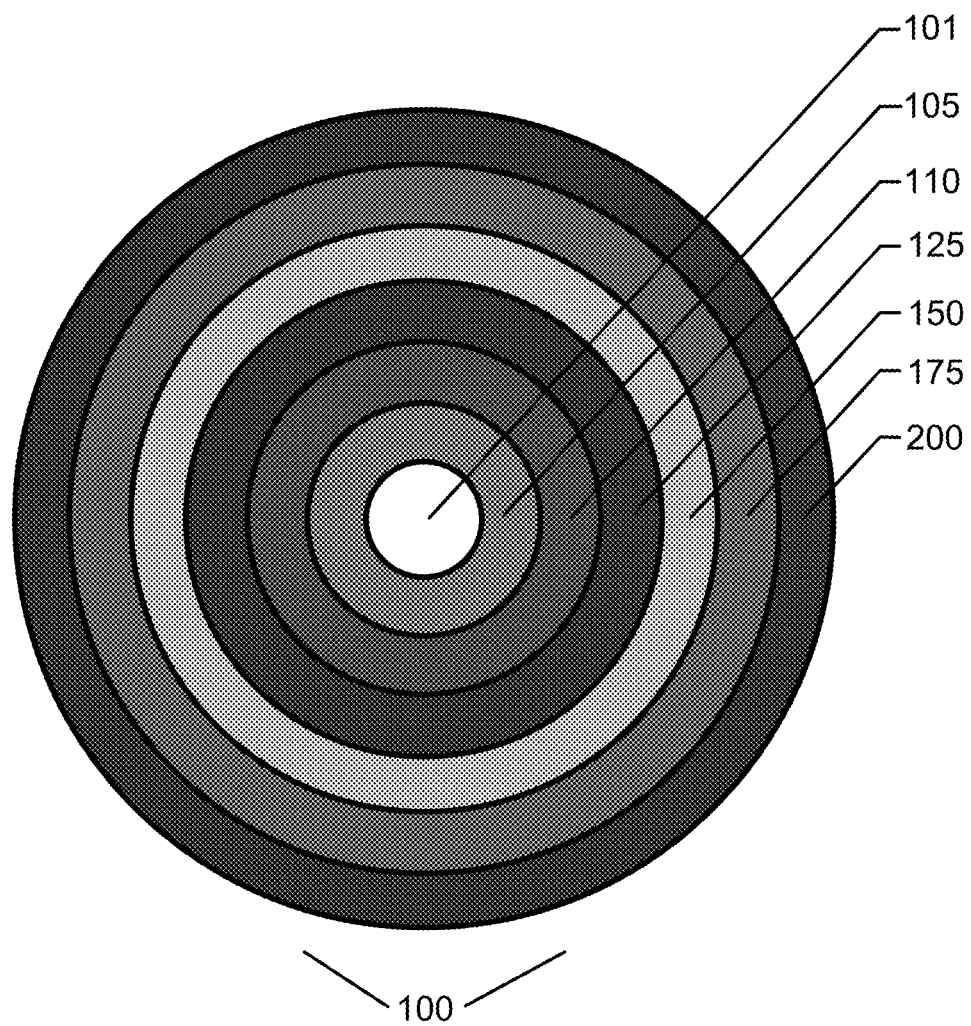
FIG. 1 is a plan view of a preferred embodiment of the current invention. The different shades of each ring are meant to indicate distinctive colors.

Referring now to FIG. 1 we see a preferred embodiment of the present invention. This embodiment 100 has an inner aperture 101, and concentric rings extending outward there from. The rings, in order from smaller inward-most to larger outermost, are: Ring 105, the smallest ring, with an inner area of 5 square centimeters; ring 110, the second smallest ring, with an inner area of 10 square centimeters; ring 125, the 3rd smallest ring, with an inner area of 25 square centimeters; ring 150, the next larger ring, with an inner area of 50 square centimeters; ring 175, the second largest ring, with an inner area of 75 square centimeters; and finally, ring 200, the largest ring, with an inner area of 100 square centimeters. Each ring is encoded with a label or other visual indicia indicating the size of its inner area.

The rings are also color-coded. From innermost ring, the color scheme number 1 currently provided is: ring 105, orange; ring 110, green; ring 125, blue; ring 150, yellow; ring 175, turquoise; and finally, ring 200, red.

The rings are used as a quick measure of the size of a wound on a patient. The operating assistant places the ring set just above the wound, and sequentially removes rings from the set, one at a time, from inward to outward, i.e. smallest to largest. After each ring removal, the operator views the wound through the central aperture. At the stage where sufficient rings have been removed to produce an aperture encompassing the entire wound, the operator stops and notes the size of the smallest remaining ring from its label or other indicia. This denotes the approximate wound size. An alternate method of application of the current invention is to remove one ring from the label and use the ring to photograph an accurate description of the wound.

Adhesive tabs corresponding to the color of the ring used can be applied to the medical chart as to reference the color. The size can also be embossed onto the tab.

A hospital is required to photograph the wound of a patient. This photograph is utilized to facilitate medical treatment and document the increase or decrease of the wound size. Observations have shown that the visual indicia tend to be too small to photograph effectively. Thus, a standardized color scheme allows for the photograph to record the wound size without reference directly to the visual indicia. The technician first arranges the rings in place around the wound. The photographer then takes color photographs. The photographs will record the wound appearance and size, through reference to the color of the rings.

Table I shows a color scheme and calibration size for a wound calibration system according to the current invention. If a color scheme, such as this one (though another will do as well—color scheme is arbitrary), is employed in standardized fashion, medical personnel can easily review photographs of the current invention in use and, from the color alone, determine wound size. Personnel can also refer to a chart, such as the one shown in Table I.

TABLE I

Ratings of wound size calibrated by the Present Invention color code

| Sq cm | Cm lineal | Color |
|---|---|---|
| 5 | 5 | Yellow |
| 10 | 10 | Blue |
| 15 | 15 | Orange |
| 20 | 20 | Magenta |
| 25 | 25 | Green |
| 50 | 50 | Purple |
| 75 | 75 | Cyan |
| 100 | 100 | Lime |

Figure 2:
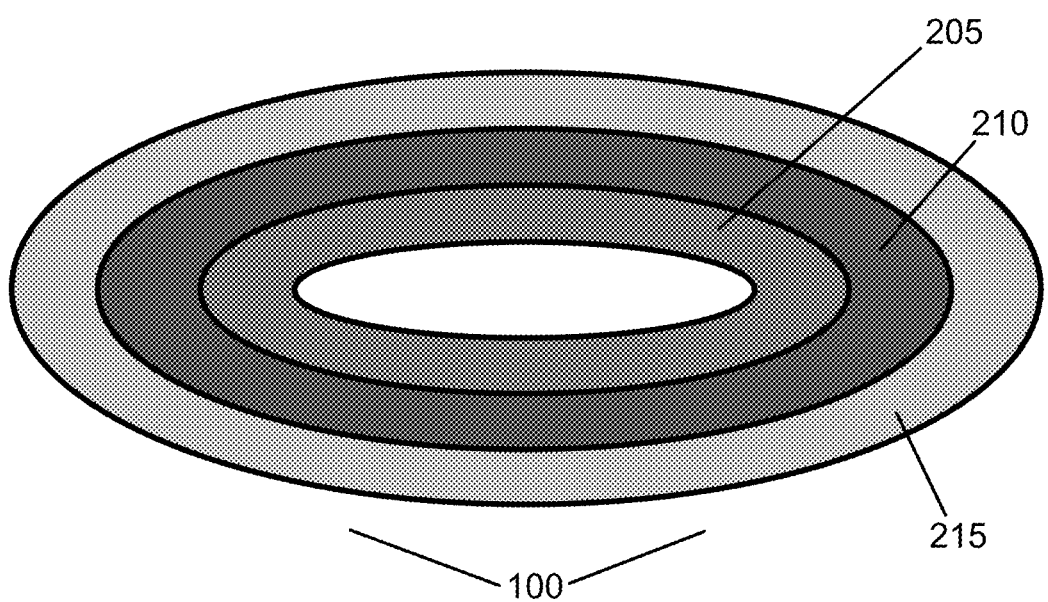
FIG. 2 is a perspective view of a simplified embodiment of the present invention, with fewer rings and different shape.

FIG. 2 shows a slightly different embodiment of a simplified form. This embodiment encompasses only 3 rings: ring 205, ring 210, and ring 215. By enlarging the width of the rings, this embodiment could be of coarser precision. For instance, ring 205 might define a width of 5 square centimeters within its inner border, while ring 210 may be as large as 25 cm, and ring 215 up to 75 cm. This might be useful in fast, approximate resolution of wound size, where speed is more important than precision and accuracy. The rings should be color coded according to a standardized scheme, so that, in the scheme of Table I, these rings would be colored as follows: ring 205, orange; 210, blue; and ring 215, cyan.

The ring set in one embodiment has adhesive backing, and thus forms a type of tape or label. It may be desirable to facilitate photography. The rings will later be removed. The rings are disposable to prevent the spread of infection from patient to patient.

Figure 11:
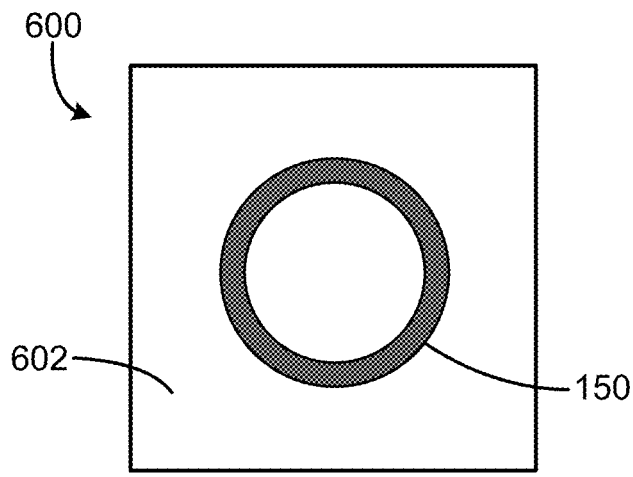
FIG. 11 illustrates an exemplary embodiment of a single ring device mounted on a backing sheet.
Figure 12:
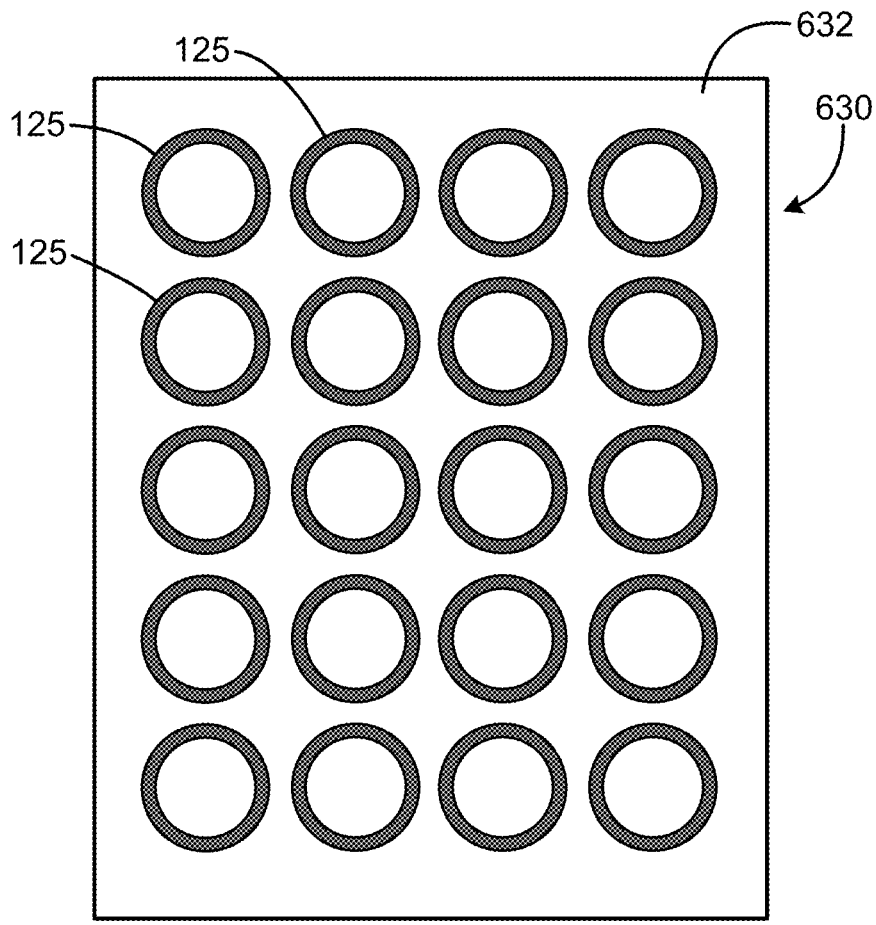
FIG. 12 shows an exemplary embodiment of multiple ring devices of the same size mounted on a single backing sheet.

Whether through the use of adhesive or other means, it is important in some embodiments of the current invention to design the rings such that they stay attached, in close contact with one another, until the inner ring or rings are removed during calibration and measurement. In one embodiment, the rings are prepared in a stack, such as for note pads. Adhesive is used to connect the rings to each other within a set, and to connect sets together in a stacked pad, from which each set is removed as needed for use. This method is equally effective for bars, or other shapes as employed in exemplary embodiments of the current invention. In other embodiments, the ring or bar devices are fabricated without adhesive backing. The devices can be held next to the wound and photographed. In other exemplary embodiments, single rings or bars can be placed on a backing sheet, or multiple rings or bars of the same size can be placed on a single sheet. FIG. 11 illustrates an exemplary embodiment 600 of a single ring device 150 mounted on a backing sheet 602. FIG. 12 shows an exemplary embodiment 630 of multiple rings 125 of the same size mounted on a single backing sheet 632.

Figure 7:
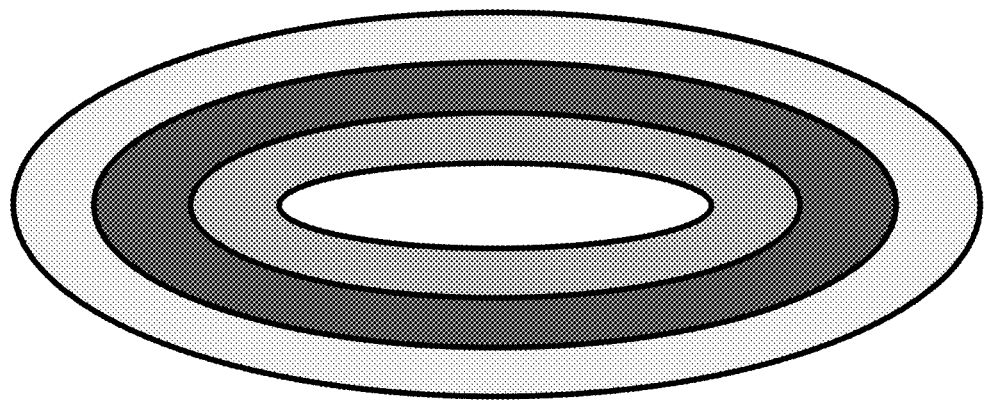
FIG. 7 shows another embodiment of the present invention utilizing ellipses.
Figure 8:
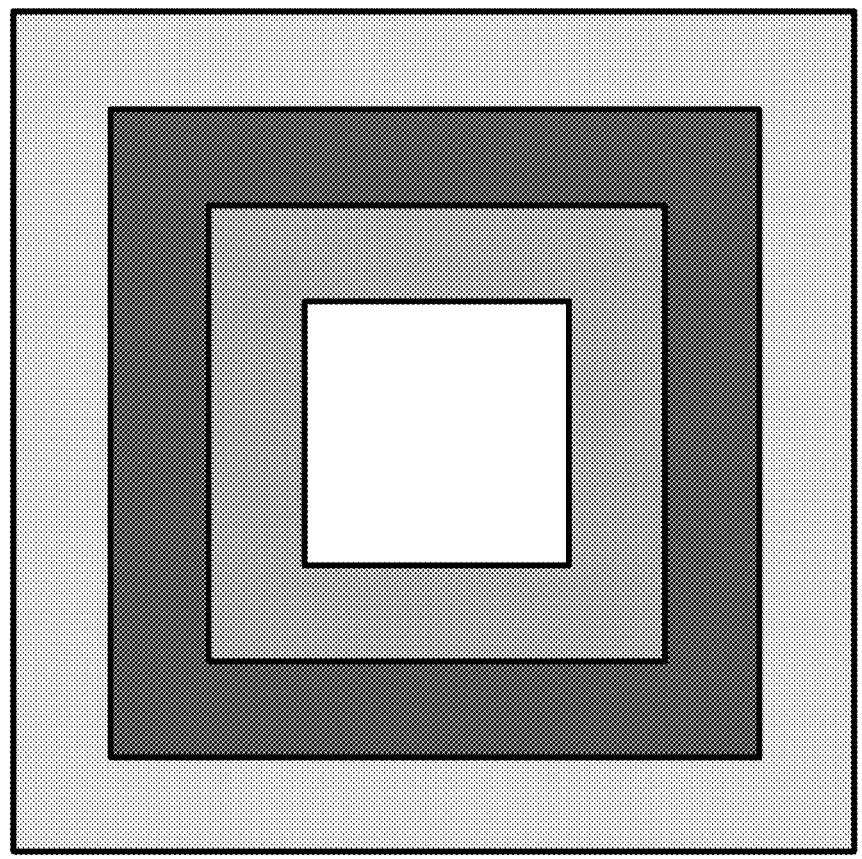
FIG. 8 shows a further embodiment utilizing squares.

It is important to note that the present invention contemplates other geometric shapes aside from circles. Concentric polygons of any closed shape could be used. Examples are nested triangles, squares, pentagons, hexagons, and octagons. FIGS. 7 and 8 show respective embodiments utilizing elliptical and square shapes, for example. Other geometric shapes or irregular shapes are possible for use as well. Circles or rings are preferred, for a circle has a constant radius at all points around the circumference of the circle. This simplifies interpretation of photographs.

Figure 3:
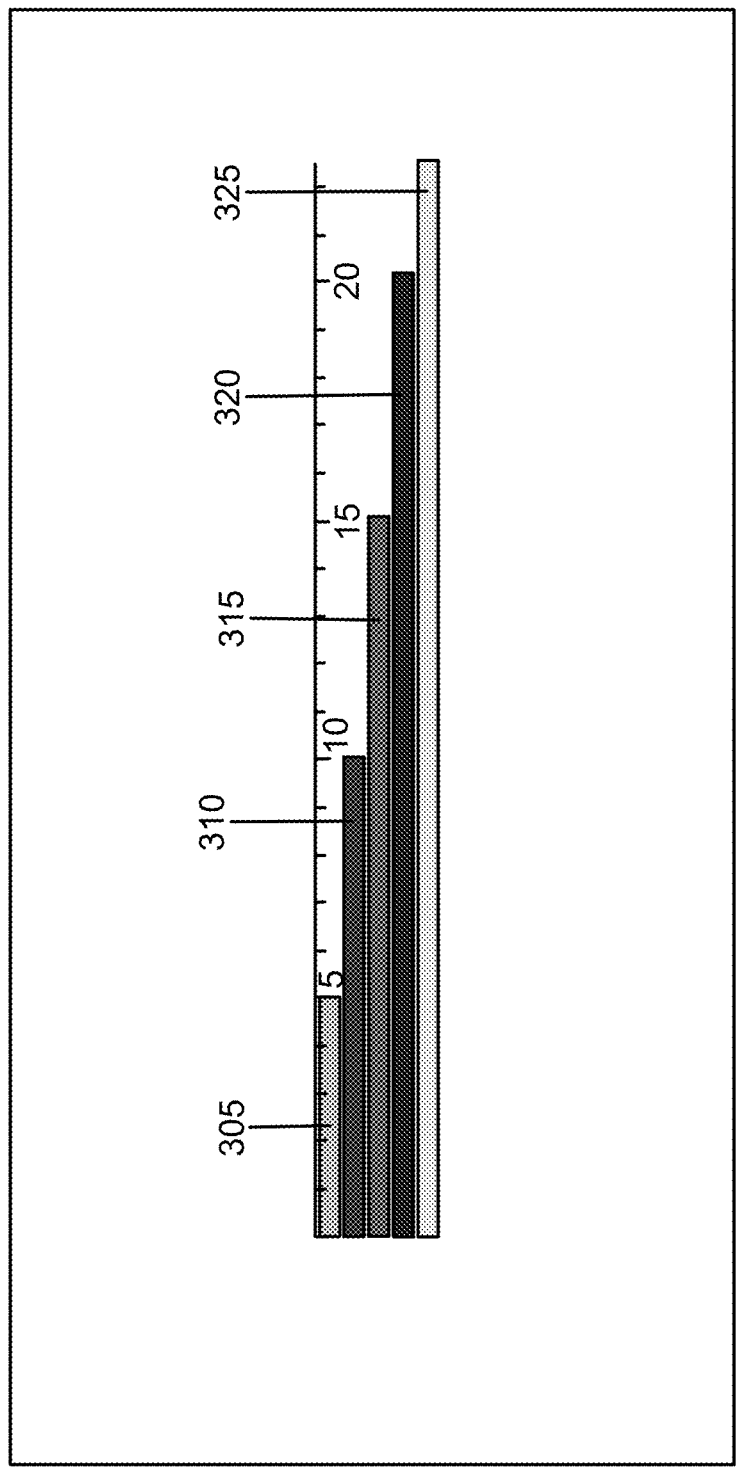
FIG. 3 is a plan view of a lineal embodiment of the present invention.

FIG. 3 illustrates an alternative form of the current invention. This embodiment is designed to measure the length of an irregular or linear wound. In this embodiment, the colored bars represent different lengths displayed with numeric ruler indicia. The bars are arranged side by side, as part of a flexible label. The bars can also be embodied as a rigid or semi-rigid composition, tape, or mounted on a transparent solid surface. FIG. 3 illustrates the bars as a label.

This embodiment can be even more simply and efficiently used than the area-calibrating rings. The operator simply applies the color bar ruler label next to the wound, and reads the ruler measurement of the wound. The bar ruler label can be applied to the patient using the adhesive that is optionally incorporated onto the backs of the bars. The colored bars next to each other offer an incremental reference for sizing. Photography may be employed as well, as described above. The color bar ruler label is held close to the wound at the point of the bar closest in length to the wound. Alternatively, all bars except the closest in length to the wound can be removed from the set, leaving only the single bar for the photograph. Also the bar ruler label can be trimmed with scissors, or the bar ruler can be perforated and torn, so that it is scaled to the size of the wound.

Although the bars are useful in visual calibration, they are essential in the photographic record, for the numerical indicia of the ruler often do not record on the camera as well as do the colors.

In the example displayed in FIG. 3, the yellow bar 305 is on top, and represents a length of 5 centimeters. Lower bars 310, 315, 320, 325 of different colors extend to 10, 15, 20, and 25 cm. The chart of Table 1 provides the details.

It will be noted that the color code displayed for the bars in the wound size length calibration system of FIG. 3 is the same as the color code displayed for the rings in Table I. Ideally, the color scheme will be the same for both, as it reduces the possibility of confusion or error in the measurement and calibration process.

However, it is certainly possible within the contemplation of the current invention to have different color schemes for linear measurement, as in bars, as distinct from area measurement, as in rings. Indeed, in alternative embodiments of the current invention, colors need not be used. Each ring need only be visually distinct from each other ring, and the same for the bars. This could be accomplished by shading, cross-hatching or other drawing techniques, or use of additional visual indicia.

We make the above point so as to reinforce two important points of the present invention. First, the color code scheme is not important in and of itself. The color red, for instance, could represent a shorter length wound, or a longer one. Red could represent a small area wound, or a larger one. The importance is in the standardization of a scheme, such that red always means the same length bar, or inner area circle or polygon. Second, the linear dimension calibration of the bars is not the same (though related) dimension as the Table I rings provide. Nevertheless, color can and will be standardized and coordinated between the rings and bars, example being the red bar can have a value of 5 linear centimeters and the red ring represents 5 sq cm.

Figure 5:
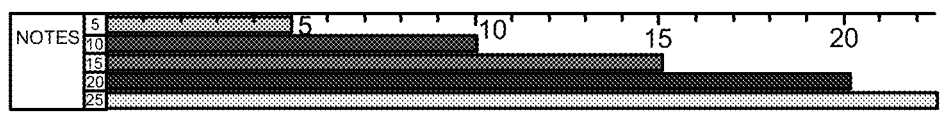
FIG. 5 is a plan view of a lineal embodiment of the present invention, with notation area depicted.

The rings or bars are preferably distributed as sets, mounted on a pad. In some embodiments, there is extra room on each sheet of the pad for writing notes, as displayed in FIG. 5, item 300. This could be valuable, for instance in dating the calibration, or making some other notes to be used in subsequent medical diagnosis. There may also be pull tabs on the bars, at the left of the zero point. Pull tabs are useful in that they carry the information of the length of the wound. The tabs are adhesive, and can easily be applied to paper surface, such as a patient's chart. This preserves useful and important information correlating to the patient's wound.

Figure 4:
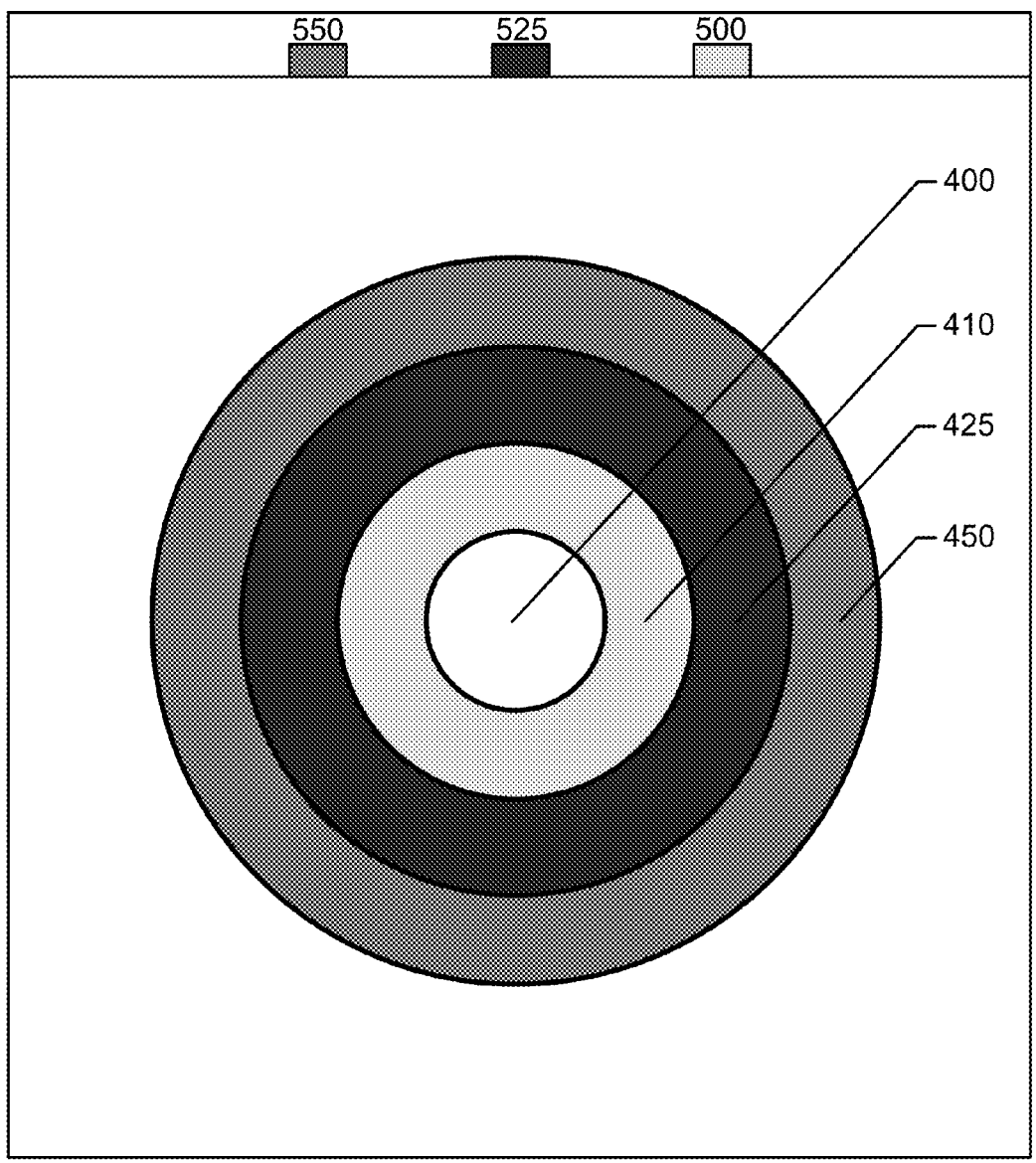
FIG. 4 shows another view of a simplified embodiment of the present invention, including the pull away colored tabs to attach to the medical chart to reflect the size of the ring used.

Similar pull tabs associated with rings are found in FIG. 4 where pull tab 550 corresponds to ring 450; tab 525 corresponds to ring 425; and tab 500 corresponds to ring 410. The pull tab shares the same color as the corresponding ring. Thus, if ring 425 is green, indicating a 25 sq cm wound area, as per Table 1, the corresponding pull tab 525 comprises the same color green.

Figure 6:
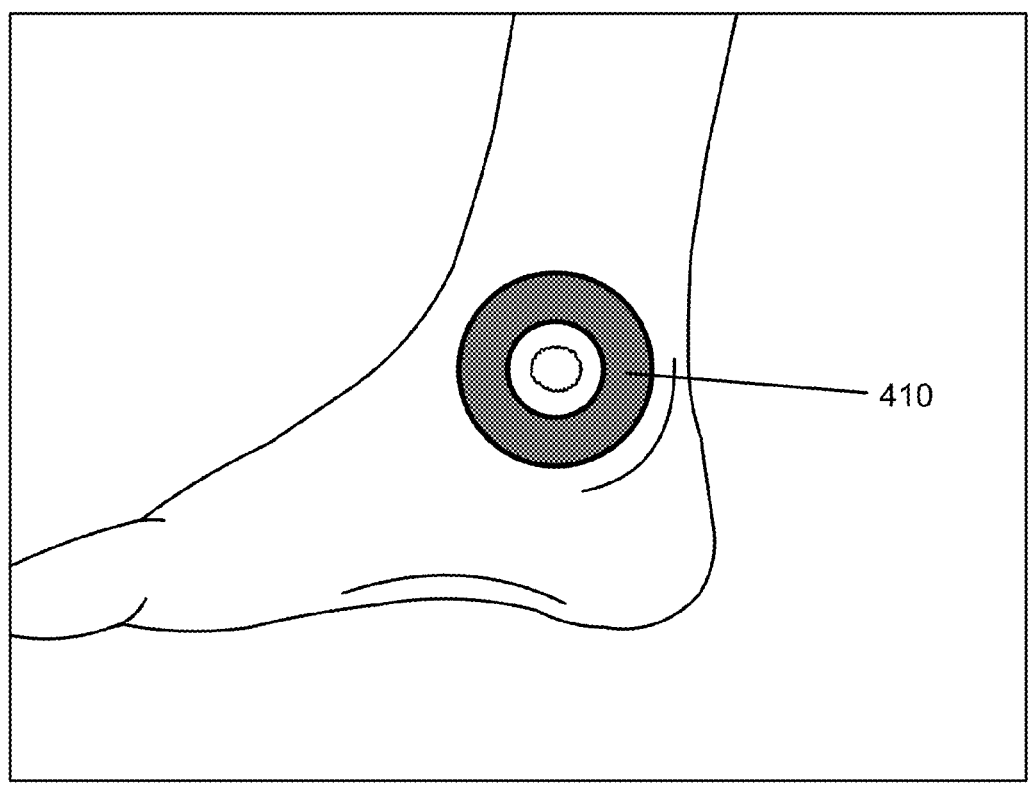
FIG. 6 shows the use of a ring of the current invention to highlight a wound on the ankle of a person.

FIG. 6 indicates the use of the present invention. In this figure, the injured area on the ankle is approximately 10 sq cm in area, and is so measured in FIG. 6 by the 10 sq cm ring, 410. The photograph is taken to record the wound, its measured size, and appearance. A pull tab could also go into the patient's file, indicating a 10 sq cm wound area.

Figure 9:
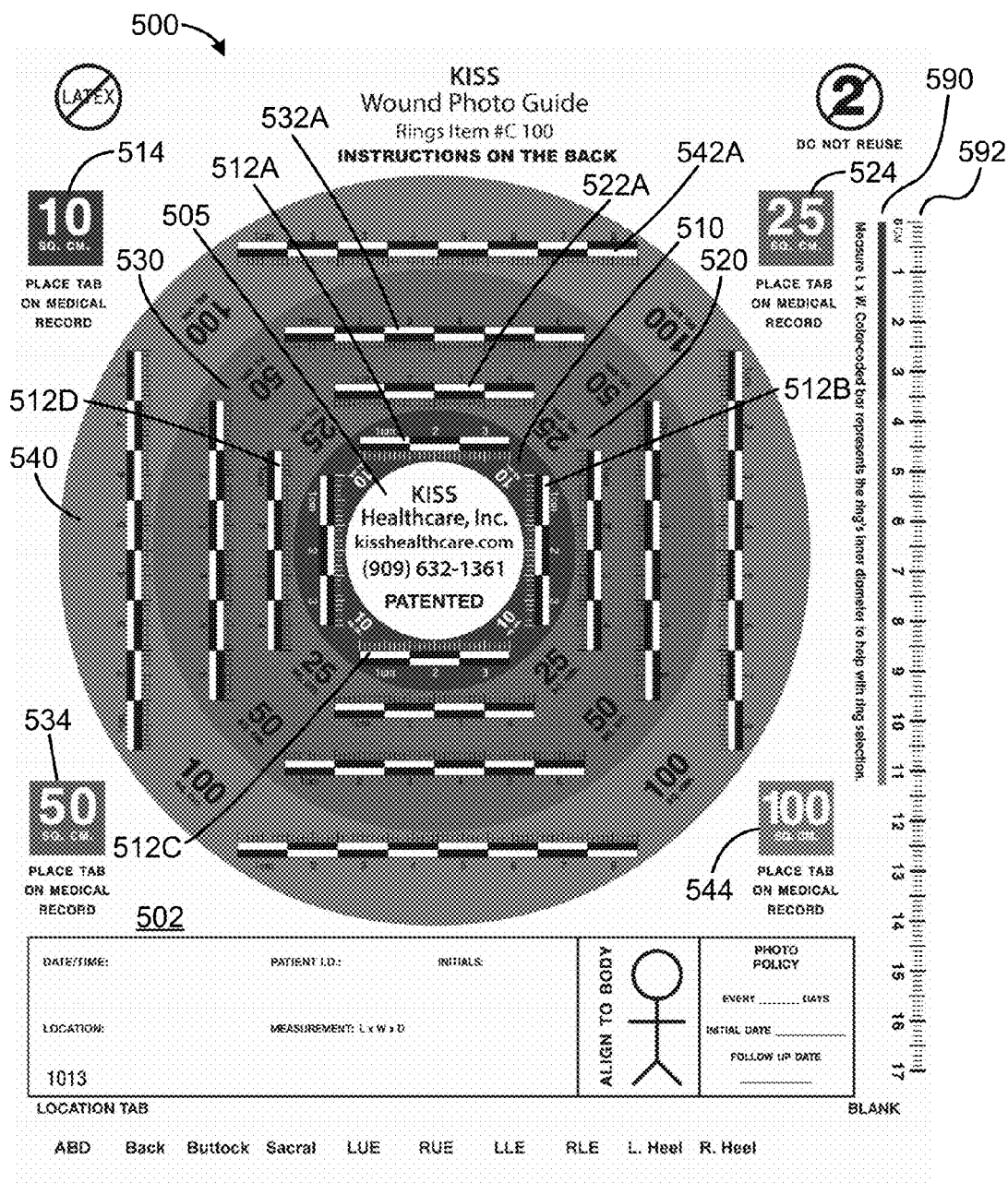
FIG. 9 illustrates a further embodiment of the invention, illustrating an exemplary photo scaling device configured to scale the area, perimeter and linear dimensions of wounds or objects at the same time.

A further embodiment is illustrated in FIG. 9, a photo scaling guide or system 500, configured to scale both the area and linear dimensions of areas of interest such as wounds or objects at the same time with one device. Exemplary users of this embodiment include photographers who are documenting an object using photography. This embodiment may also be used in health care to photograph wounds for the medical record. In forensics, the embodiment may be used by an investigator photographing wounds, blood splatters or other evidence for crime scene documentation. Insurance industries may use the embodiment to photograph evidence used in claims. Uses and applications are not limited to these exemplary applications.

The system 500 utilizes linear scales or "rulers" on the rings, ellipses, polygons or other closed shapes or configurations, as described above regarding the embodiments of FIGS. 1-8. The area inside the closed device allows the investigator to compare one area to another. The ruler allows the investigator to determine length and width more accurately. The rulers can be printed on the closed device in any configuration, such as rings, ovals, ellipses, square, rectangular, hexagonal, and the like, examples of which are shown in FIGS. 1-8. The system 500 of FIG. 9 employs concentric ring devices 510, 520, 530, 540 and 550, similar to the embodiment of FIG. 1.

In the exemplary embodiment of FIG. 9, the area inside each closed device is displayed in visible alphanumeric markings on the device facing outwards, at four spaced locations. The outwards configuration allows the device to be applied around an object so that, no matter how it is placed, the user may readily read the area designation, and there is no predetermined alignment. For this example, ring device 510 surrounds a 10 cm$^2$ area, device 520 a 25 cm$^2$ area, device 530 a 50 cm$^2$ area and device 550 a 100 cm$^2$ area, as indicated by the markings. In this embodiment, the ring devices are adhesively backed, and arranged concentrically on a backing sheet 502 for storage prior to use. Each device may be selectively removed from the backing sheet for application to a patient or object in use. Alternatively, each device may be arranged on a separate backing sheet, i.e. one device per backing sheet.

In this embodiment, the closed devices 510, 520, 530, 540 and 550 are also color coded, in the same fashion as described above regarding the embodiment of FIG. 1, so that each color corresponds to a predetermined area. The color coding may follow the convention set out in Table 1 above, or another color coding.

The system 500 further includes, in this embodiment, scales or ruler indicia, reflecting a linear length measurement, for each closed device. In the example of ring devices illustrated in FIG. 9, the rulers are printed over the ring device with four sides, a virtual square. For example, rulers 512A, 512B, 512C and 512D are printed on the inner ring 510, and reflect a dimension close or equal to the interior diameter of the ring. Each of the other rings also has four rulers, e.g. 522A, 532A, 542A and 550A. The rulers opposite of each other line up with each other where they are parallel to each other and the lengths on one ruler match up with the opposite ruler, example being the 1 cm position lines up with the opposite 1 cm point on the ruler.

Figure 10:
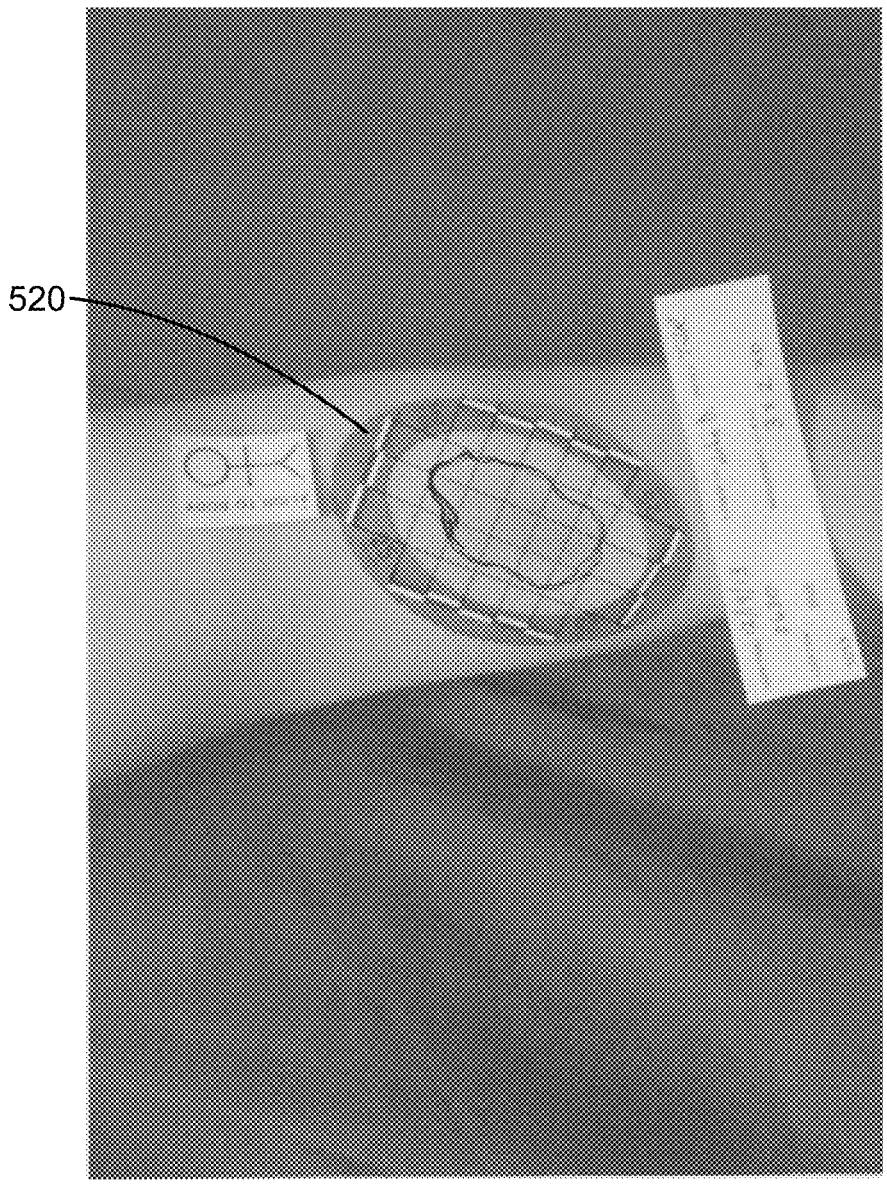
FIG. 10 diagrammatically illustrates a photograph, illustrating how a ring device may be used, to surround a wound area on a patient's body, to calibrate and measure the wound size.

FIG. 10 diagrammatically illustrates a photograph, illustrating how a ring device may be used, to surround a wound area on a patient's body, to calibrate and measure the wound size. The ring device 520 of the set shown in FIG. 9 is depicted in place on a patient's arm, surrounding a wound diagrammatically indicated by an irregular closed outline. A grid calibrated to the linear scale has been defined on the photograph, and can further assist in analysis of the wound size. The grid can be defined by a software algorithm or application such as "Photoshop," or manually on a printed version of the photograph.

The ring system 500 in one embodiment has adhesive backing, and are adhered to a backing sheet 502, thus forming a type of tape or label. The individual ring devices will later be removed from the backing sheet for application to a patient's body or other object to be photographed. The rings are disposable to prevent the spread of infection from patient to patient.

Whether through the use of adhesive or other means, in an exemplary embodiment, the rings of the system 500 are designed such that they stay attached, in close contact with one another, until the individual ring or rings is removed for application to a subject. Adhesive may be used to connect the rings to each other within a set. In other embodiments, the rings may be arranged side-by-side on a backing sheet, or each ring on a separate backing sheet.

The system 500 may be fabricated of various materials, including paper, plastic, metal, glass or the like. The individual ring devices can bend to the curvature of the body or object on which it is placed. When curvature is present, the rulers provide length and width perspective given the depth of the object, or varying distance from the camera. This allows for a more quantitative analysis of the object. It allows for analysis of the entire object or parts of the object. The investigator can also use the rulers opposite from each, top and bottom, right and left, to study how the size of an object changes with distance from camera. The advantage of this configuration is that it gives the investigator the linear perspective all around the object.

An added feature of this embodiment 500 of the invention is a scale 590 next to a ruler indicia 592 on a side of the sheet adjacent the outer device 540. This scale is color-coded, with the color of the scale adjacent the ruler indicia representing the inner diameter of the rings on the sheet. This aids the photographer in selecting the correct ring size when they use the ruler to measure the wound size and scale its perimeter. In this exemplary embodiment, the correct ring is dependent on the inner diameter of the individual color-coded rings. Placing the scale 590 next to the ruler 592 allows for quick assessment of the ring size needed for a particular application. In this exemplary embodiment, the scale and ruler do not detach from the backing sheet 502, and may be printed onto the sheet.

The system 500 also includes color-coded tabs 514, 524, 534, 544, which may be detached from the backing sheet for placement on the patient's chart, or other chart or log.

In other embodiments, the ring or scale devices may be a single color, and the size indication provided by the scale and/or visible alphanumeric markings on each device. For example, the individual ring devices of the embodiment of Claim 9 may alternatively be formed of an opaque white coloration, with the visible alphanumeric markings as well as the scales in a contrasting color to show up in a photographic.

The uses of the present invention are not limited to the medical field. Forensic investigators will also find the invention useful. For instance, crime scene investigators could measure areas of interest, such as wounds, scars, or markings on bodies, or on other surfaces, or bullet holes in surfaces (e.g. to determine caliber or size of the bullet) through the use of the rings or bars of exemplary embodiments of the current invention. Photographs could be taken, and the information recorded for subsequent study. Investigators in accident investigations could make similar use of the present invention, for example to calibrate areas at a crash site.

While the invention has been described in connection with a preferred embodiment or embodiments, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A photo scaling guide configured to scale both the actual linear dimension and the area characteristics of an object area of interest with one device, the one device comprising:
    a closed device having an actual area size corresponding to a predetermined area characteristic value, said closed device further including at least one linear ruler indicia indicating a predetermined actual length characteristic value associated with the device, the closed device configured to adhere to the object;
    said closed device defining a label removably adhered to a backing sheet;
    said closed device having a closed configuration surrounding a predetermined open area indicated by said unique visual indicator, wherein the open area is a space bordered by the closed device, the closed device configured for application to the object after removal from the backing sheet to surround the object area of interest and with the open area overlying without contacting the object area of interest;
    said closed device having a unique visual indicator uniquely representing said predetermined area characteristic value according to a predetermined visual indicator code scheme representative of a plurality of different size characteristic values; and
    wherein the device visual indicator is a color indicating said size characteristic value, and said code scheme includes a plurality of different colors each identifying a particular unique size characteristic.

2. The guide of claim 1 wherein said closed device is a ring circumscribing said predetermined open area, and said at least one linear ruler indicia is defined on said ring.

3. The guide of claim 2, wherein the ring is adapted to surround a wound, wherein the object is a wound on a person.

4. The guide of claim 2, wherein said at least one linear ruler indicia comprises four linear ruler scales with graduated markers, equally spaced from each other about the ring and each having a length substantially equal to an interior diameter of the ring.

5. The guide of claim 4, wherein the four ruler indicia at least partially sides of a square.

6. The guide of claim 1, further comprising a visible alphanumeric marking on the closed device, said marking indicative of a value of said open area.

7. The guide of claim 1, further comprising a removable pull tab containing indicia indicating said area characteristic associated with said device.

8. The guide of claim 1, the closed device having an adhesive backing for adhering to the backing sheet prior to use, and for attaching the device to a patient or object for use in photographing the object area of interest to document its size.

9. The guide of claim 8, further comprising a linear scale on the backing sheet and positioned next to the closed device, the linear scale comprising graduated markers.

10. A set of guides, each one device as in claim 1 and comprising a ring circumscribing a predetermined open area, and of different diameters so as to be concentrically mounted on a backing sheet for selective removal for application to a patient or object.

11. A system configured to scale both the actual linear dimension and the area characteristics of an area of interest of an object with one device, the system comprising:
    a device having an actual area size corresponding to a predetermined area characteristic value, said device further including at least one linear ruler indicia indicating a predetermined actual length, the device configured to be arranged over the object:
    said device having a closed configuration surrounding a predetermined open area indicated by said unique visual indicator;
    said closed device defining a tape or label removably adhered to a backing sheet, and configured for placement on the object with the predetermined open area overlying without contacting the object area of interest;
    said device having a unique visual indicator uniquely representing said predetermined area characteristic value according to a predetermined visual indicator code scheme representative of a plurality of different size characteristic values; and
    wherein the device visual indicator comprises a visible alphanumeric marking on the one device, said marking indicative of a value of said area size.

12. The system of claim 11 wherein said device is a ring circumscribing said predetermined open area, and said at least one linear ruler indicia is defined on said ring.

13. The system of claim 12, wherein the ring is adapted to surround a wound, wherein the object region of interest is a wound on a person.

14. The system of claim 11, wherein said at least one linear ruler indicia comprises four ruler indicia, equally spaced from each other about or adjacent an outer periphery of the device and each having a length substantially equal to said actual length dimension.

15. The system of claim 11, wherein the device is fabricated of a flexible material configured to conform to a curvature of the object.

16. The system of claim 11, further comprising an adhesive backing for attaching the device to a patient or device for use.

17. The system of claim 16, further comprising a linear scale on the backing sheet and positioned next to the one device.

18. The system of claim 1, wherein the device is fabricated of a flexible material which can bend to the curvature of the body or object to which the device is applied.

* * * * *